(12) United States Patent
Rich et al.

(10) Patent No.: US 10,420,490 B2
(45) Date of Patent: Sep. 24, 2019

(54) SYSTEMS AND METHODS FOR PHYSIOLOGICAL MONITORING USING MULTIPLE SIGNAL PROCESSING DEVICES

(71) Applicant: XHALE ASSURANCE, INC., Gainesville, FL (US)

(72) Inventors: David Rich, Glastonbury, CT (US); Andrew Kersey, Wallingford, CT (US); Sean Cohen, Gainesville, FL (US); Richard Melker, Gainesville, FL (US)

(73) Assignee: XHALE ASSURANCE, INC., Gainesville, FL (US)

(*) Notice: Subject to any disclaimer, the term of this patent is extended or adjusted under 35 U.S.C. 154(b) by 0 days.

(21) Appl. No.: 14/310,569

(22) Filed: Jun. 20, 2014

(65) Prior Publication Data

US 2015/0073233 A1   Mar. 12, 2015

Related U.S. Application Data

(60) Provisional application No. 61/874,722, filed on Sep. 6, 2013.

(51) Int. Cl.
*A61B 5/00* (2006.01)
*A61B 5/08* (2006.01)
*A61B 5/1455* (2006.01)

(52) U.S. Cl.
CPC ............ *A61B 5/14551* (2013.01); *A61B 5/08* (2013.01); *A61B 5/7282* (2013.01)

(58) Field of Classification Search
CPC ..... A61B 5/0205; A61B 5/02427; A61B 5/04; A61B 5/0816; A61B 5/14552; A61B 5/721; A61B 5/7282
USPC ......... 600/300, 301, 323, 484, 529; 128/898
See application file for complete search history.

(56) References Cited

U.S. PATENT DOCUMENTS

| | | | | |
|---|---|---|---|---|
| 4,802,486 | A | * | 2/1989 | Goodman .......... A61B 5/02416 600/324 |
| 5,924,979 | A | * | 7/1999 | Swedlow et al. ............. 600/300 |
| 6,648,820 | B1 | * | 11/2003 | Sarel .................... A61B 5/0002 128/903 |
| 8,545,417 | B2 | | 10/2013 | Banet |
| 2003/0225337 | A1 | * | 12/2003 | Scharf ................ A61B 5/14551 600/508 |
| 2007/0270699 | A1 | * | 11/2007 | Crabtree et al. .............. 600/500 |
| 2009/0018409 | A1 | * | 1/2009 | Banet .................. A61B 5/0408 600/301 |
| 2009/0105556 | A1 | * | 4/2009 | Fricke et al. ................. 600/301 |
| 2010/0113898 | A1 | | 5/2010 | Kim |

(Continued)

FOREIGN PATENT DOCUMENTS

WO   WO2004075746  A2 *  9/2004  ............. A61B 5/024

*Primary Examiner* — Nathan J Jenness (57) ABSTRACT

Provided according to embodiments of the invention are systems for monitoring a physiological state of an individual that include a PPG sensor, which optionally includes an auxiliary physiological sensor integrated with or connected thereto; a first signal processing device in electronic communication with the PPG sensor, whereby the PPG sensor transmits PPG signals to the first signal processing device; and a second signal processing device that detects at least a portion of the signals transmitted by the PPG sensor to the first signal processing device, at least a portion of signals transmitted by the auxiliary physiological sensor, or both. Related methods are also provided herein.

8 Claims, 7 Drawing Sheets

(56) References Cited

U.S. PATENT DOCUMENTS

| | | | |
|---|---|---|---|
| 2010/0204550 A1* | 8/2010 | Heneghan et al. | 600/301 |
| 2010/0312075 A1* | 12/2010 | McGonigle et al. | 600/301 |
| 2011/0028801 A1* | 2/2011 | Koh | 600/301 |
| 2011/0270048 A1* | 11/2011 | Addison et al. | 600/301 |
| 2012/0029304 A1* | 2/2012 | Medina | A61B 5/0002 600/300 |
| 2012/0253156 A1 | 10/2012 | Muhlsteff | |
| 2012/0310062 A1* | 12/2012 | Li et al. | 600/328 |
| 2013/0079606 A1 | 3/2013 | McGonigle | |
| 2013/0253334 A1* | 9/2013 | Al-Ali | A61B 5/002 600/476 |
| 2015/0205931 A1* | 7/2015 | Wang | A61B 5/746 702/19 |

* cited by examiner

SYSTEMS AND METHODS FOR PHYSIOLOGICAL MONITORING USING MULTIPLE SIGNAL PROCESSING DEVICES

FIELD OF THE INVENTION

The present invention relates to biological sensors, and in particular, to photoplethysmography sensors. The present invention also relates to mammalian respiration and ventilation and methods and devices for monitoring the same.

BACKGROUND OF THE INVENTION

Photoplethysmography, or "PPG", is an optical technique for detecting blood volume changes in a tissue. In this technique, one or more emitters are used to direct light at a tissue and one or more detectors are used to detect the light that is transmitted through the tissue ("transmissive PPG") or reflected by the tissue ("reflectance PPG"). The volume of blood, or perfusion, of the tissue affects the amount of light that is transmitted or reflected. Thus, the PPG signal may vary with changes in the perfusion of the tissue.

In most hospital settings, PPG is only used for measuring blood oxygen saturation, and so oximeter or multiparameter monitors are typically only configured to process the PPG signals to determine blood oxygen saturation measurements. However, the PPG signal may also vary with respiration as the PPG signal is responsive to changes in intrathoracic pressure. Thus, PPG remains a promising technique for monitoring respiration in individuals, particularly in spontaneously breathing individuals, when conventional respiration monitoring techniques such as capnometry are often not sufficiently reliable.

SUMMARY OF THE INVENTION

Provided according to embodiments of the present invention are systems for monitoring a physiological state of an individual. Such systems may include a PPG sensor, which optionally includes an auxiliary respiration sensor integrated with or connected thereto; a first signal processing device in electronic communication with the PPG sensor, whereby the PPG sensor transmits PPG signals to the first signal processing device; and a second signal processing device that detects at least a portion of the signals transmitted by the PPG sensor to the first signal processing device, at least a portion of signals transmitted by the auxiliary respiration sensor, or both. In some embodiments, the second signal processing device detects at least a portion of the PPG signals sent from the PPG sensor to the first signal processing device without disrupting the operation of the first signal processing device. In some cases, the second signal processing device is independent from the first signal processing device. Further, in some embodiments, the at least a portion of the PPG signals that are detected by the second signal processing device are amplified before processing by the second signal processing device.

In some embodiments of the invention, the second signal processing device processes the at least a portion of the PPG signals to determine a physiological parameter or event, in some cases, in real time, and in some cases, the physiological parameter or event is a physiological parameter or event not determined by the first signal processing device. In some embodiments, the physiological parameter or event is determined based on the at least a portion of the PPG signals from the PPG sensor and the at least a portion of the signals from the auxiliary physiological sensor. In some embodiments, the PPG sensor is configured to transmit a first PPG signal stream to the first signal processing device and a second PPG signal stream to the second signal processing device.

In some embodiments of the invention, the first signal processing device is part of or in communication with a first display monitor and the second signal processing device is part of or in communication with a second display monitor. In some embodiments of the invention, the second signal processing device further detects input signals sent from the first signal processing device to the PPG sensor, for example, input signals for energizing an LED in the PPG sensor.

In some embodiments of the invention, the PPG sensor transmits the PPG signals to the second signal processing device, which then transmits at least a portion of the PPG signals to the first signal processing device. In some cases, the second signal processing device processes at least a portion of the PPG signals, for example, to determine a physiological parameter, before transmitting the PPG signals to the first signal processing device.

In some embodiments of the invention, when the first signal processing device is disconnected from the PPG sensor, the PPG signals are then automatically transmitted to the second signal processing device. In some embodiments, a third signal processing device in communication with the second signal processing device, wherein the third signal processing device comprises a monitor that displays at least one physiological parameter or event determined by the at least a portion of PPG signals sent from a PPG sensor, the at least a portion of signals from an auxiliary respiration detector integrated with or connected to the PPG sensor, or both.

Also provided according to embodiments of the invention are methods of physiological monitoring with a system according to an embodiment of the invention. Such methods include detecting, with a second signal processing device, at least a portion of PPG signals sent from a PPG sensor to a first signal processing device, at least a portion of signals from an auxiliary respiration detector integrated with or connected to the PPG sensor, or both.

BRIEF DESCRIPTION OF THE DRAWINGS

The following drawings are provided to illustrate various aspects of the present inventive concept and are not intended to limit the scope of the present invention unless specified herein.

DETAILED DESCRIPTION OF EMBODIMENTS OF THE INVENTION

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers refer to like elements throughout the specification.

It will be understood that, although the terms first, second, etc. (or primary, secondary, etc.) may be used herein to describe various elements, these elements should not be limited by these terms. These terms are only used to distinguish one element from another. Thus, a first element discussed below could be termed a second element without departing from the teachings of the present invention.

Provided according to embodiments of the present invention are methods and systems for monitoring a physiological state of an individual. In general, PPG sensors are electrically connected to an oximeter, multiparameter monitor or other signal processing device. While such systems may be useful for the conventionally monitored physiological parameters, it may be difficult to incorporate new technologies into the conventional monitoring equipment available in most hospitals or other care settings. In the case of photoplethysmography, PPG signals are conventionally used to determine blood oxygen saturation, but the same signals may also be used in newer technologies, such as those that use the PPG signal to monitor respiration. The present invention allows signals from one device to be used in both a traditional manner with the existing equipment and with new technologies by tapping into the signal pathway with an alternate signal processing device. The present invention also allows for the use of combination sensors, whereby some of the signals from the sensor are transmitted to the conventional monitors (e.g., a first signal processing device) while other signals from the combination sensor are transmitted to one or more additional signal processing device for additional or alternative processing.

Thus, provided according to some embodiments of the invention are systems for monitoring a physiological state of an individual. Such systems include a PPG sensor, which optionally includes an auxiliary respiration sensor integrated with or connected thereto; a first signal processing device in electronic communication with the PPG sensor, whereby the PPG sensor transmits PPG signals to the first signal processing device; and a second signal processing device that detects at least a portion of the signals transmitted by the PPG sensor to the first signal processing device, at least a portion of signals transmitted by the auxiliary respiration sensor, or both.

The Individual

The systems and methods described herein are used for monitoring the physiological state of an individual. As used herein, an individual, also referred to as a patient, includes any mammal, including humans of any age. The individual may be monitored in any care setting including, but not limited to, hospitals (e.g., operating room (OR), intensive care unit (ICU), general care floors, or during transport therein); nursing homes, medical offices, medical transport, and homes. Furthermore, the methods, devices and systems described herein may be useful for both spontaneously breathing patients and mechanically ventilated patients.

The PPG Sensor and Optional Auxiliary Respiration Sensor

The systems and methods described herein use at least one signal processing device to process and analyze PPG signals from at least one PPG sensor to determine at least one physiological parameter or event in the individual. The PPG signals processed by the signal processing devices may be obtained in any suitable manner and at any suitable physiological site. However, in some embodiments, the PPG signal will be obtained at a site at or on the head of the individual (also referred to herein as a "central source site"). Such sites include, but not are limited to, the ear, nose (e.g., the nasal alar, nasal septum or nasal columella), forehead, cheek, lip, ophthalmic artery, and pre-auricular or post-auricular sites.

The PPG signals may be obtained by securing at least one PPG sensor (also referred to as a PPG probe) to the individual. The term "secure" means to attach sufficiently to the tissue site to allow for a suitable PPG signal to be generated. In some cases, the sensor is configured to secure onto a tissue site such that no additional support is necessary to allow for a suitable PPG signal to be reliably generated. However, in some cases, the sensor may be secured with the aid of an external support, for example, an additional structural support, a wire or cord, or an adhesive product such as tape. Such supports may be desirable to stabilize the sensor to prevent against signal loss, for example, due to the patient's movement, or due to movement (e.g., jostling, pulling, pushing) of the sensor or a cable attached thereto.

The PPG sensors include one or more components that emit light, and such components will be referred to herein as "emitters." As used herein, the term "light" is used generically to refer to electromagnetic radiation, and so the term includes, for example, visible, infrared and ultraviolet radiation. Any suitable type of emitter may be used, but in some embodiments, the emitter is a light-emitting diode (LED). In particular embodiments, a first emitter emits light at a first wavelength, and a second emitter emits light at a second wavelength. In some cases, a single emitter may emit light at a first wavelength and a second wavelength. One or more photodetectors, also referred to as "detectors", are also included in the PPG sensor. The detector is configured to detect light from an emitter, and this detected light generates a PPG signal. Any suitable photodetector may be used. However, examples of photodetectors include photodiodes, photoresistors, phototransistors, light to digital converters, and the like. The PPG signals are monitored over time and the PPG signals generated by the photodetector(s) may be referred to as "PPG signals," "a PPG signal stream," or "a PPG waveform."

In particular embodiments of the invention, the PPG sensor(s) may transmit more than one PPG signal stream to the first and additional signal processing devices. One or more additional emitters and/or one or more additional detectors may be included on the PPG sensor so that a first PPG signal stream may be transmitted to a first signal processing device and a second PPG signal stream may be transmitted directly to one or more additional signal processing devices. Additional signal streams and signal processing devices may also be present. This obviates the need for the second signal processing device to use the first PPG signal stream because may provide a separate but substantially identical PPG signal stream transmitted directly to the second signal processing device. The two or more PPG signal streams, in some embodiments, may be part of the same signal path such as a cable or wire, but can be separately transmitted to the respective signal processing devices at a connector, splitter or other connector in the cable.

In some embodiments of the invention, the PPG sensor may be integrated with or connected to an auxiliary respiration sensor. The PPG signals may themselves be used to monitor respiration, such as described, for example, in U.S. Pat. No. 7,785,262 and U.S. Patent Application Publications 2013/0276785 and 2013/0296823, which are incorporated herein by reference in their entirety. Other methods of monitoring respiration from PPG signals are known and may be used in embodiments described herein. The auxiliary respiration sensor may be used either to monitor respiration by itself, whereby the PPG signals are only used to monitor blood oxygen saturation and/or other conventional parameters, or signals from the auxiliary respiration sensor may be used in combination with the PPG signals to monitor respiration. The respiratory data from the auxiliary respiration sensor can be compared or combined with the information from the PPG signals to provide greater certainty regarding the respiratory events or parameters or to provide additional respiratory data not available with the PPG signals. The PPG sensor and the auxiliary respiration sensor may share a signal pathway such as a cable, wire and the like, or they may be transmitted separately to a signal processing device for processing and/or analysis.

Auxiliary respiration sensors include, but are not limited to, nasal air flow sensors, nasal pressure sensors, capnometers, thermistors, acoustic sensors, differential pressure transducers, chest or abdominal bands, and the like. In some cases, both the PPG sensor(s) and the auxiliary respiration sensor(s) are situated at the nose, and in some cases, a single device or system (e.g., an array) may include both the PPG sensor(s) and the auxiliary respiration sensor(s).

In particular embodiments, the auxiliary respiration sensor may detect respiratory airflow or temperature changes at the nostril, such as with a thermistor. For example, during inspiration, a thermistor placed at the nostril detects a relative decrease in temperature compared to exhalation since, in most situations, body temperature, and therefore exhaled breath temperature, is higher than ambient temperature. Thus, detection of changes in temperature may be a suitable means to determine respiratory air flow and therefore, respiratory rate. Air flow from one or both nostrils may be monitored and, in some cases, be compared with the PPG information.

As another example, capnometry may provide a number of respiratory parameters. Such parameters may generally be reliably used for monitoring adequacy of ventilation if the patient is intubated. Unfortunately both hyper- and hypoventilation in patients may cause the capnometry results may be unreliable. However, in some cases, capnometry may be useful as an auxiliary respiration sensor to detect the respiratory airflow and, in some cases, may be used to validate the PPG-based (or other) respiratory determinations.

Other physiological sensors may be present in some embodiments of the invention. For example, the PPG sensor may be integrated with or connected to physiological sensors including, but not limited to, oxygen sensors, pH sensors, blood pressure sensors, breath constituent sensors, blood constituent sensor, heart rate or activity sensors (e.g., ECG sensors) and depth of anesthesia sensors. Signals from such sensors may be transmitted and processed in addition to, or in lieu of, the signals from the auxiliary respiration sensor. Thus, in some embodiments, the first or additional signal processing devices may process signals from one or more of these additional physiological sensors in order to determine a physiological parameter or event. It is to be understood that in any embodiments described herein, the auxiliary respiration detector may be replaced with the "other physiological sensors."

Signal Processing Devices

As described above, at least one PPG sensor transmits PPG signals to a first signal processing device, and one or more additional signal processing device(s) detect those PPG signals. Furthermore, in some cases, the one or more additional signal processing device(s) detect any signals (e.g., input signals) sent by the first signal processing device to the PPG sensor(s). The one or more additional signal processing device(s) generally also detect signals from an auxiliary respiration sensor when present, but in some cases, the signals from the auxiliary respiration sensor may be transmitted to the first signal processing device for processing therein.

The signal processing devices include any device that can receive physiological signals and process them to determine a physiological parameter, physiological event or other measure of the physiological state of the individual. The terms first, second, third, etc. may be used with respect to the various signal processing devices, but these terms are used only to distinguish the different devices from one another. As described herein, the "first" signal processing device is typically, but not necessarily, the more traditionally used device, such as an oximeter, multiparameter monitor and the like. The second (or additional) signal processing device(s) are typically, but not necessarily, independent device(s) that can be connected at any point between the sensor(s) and the first signal processing device. Thus, in some cases, the additional signal processing device(s) may be integrated into or connected to a cable between the sensor(s) and the first signal processing device. In other cases, the additional signal processing devices may be in wireless communication with the sensor(s) and, in some cases, the first signal processing device. The signal processing devices typically have a display (also referred to as a "monitor"), integrated with or communicatingly connected thereto, which displays the waveform(s), processed data or parameters to the caregivers or the individual, but this is not required. In some embodiments, the first signal processing device may be disconnected from the sensor(s) and the additional signal processing device(s) can take over the processing or parameter monitoring from the first signal processing device and become the primary or only signal processing device monitoring the individual.

The additional signal processing device(s) detect the signals transmitted by at least one of the sensors to the first signal processing device. The term "detect" includes, but is not limited, to receiving and retransmitting, diverting or otherwise monitoring the signal that is sent by the sensor(s). In some cases, a small portion of the signal from the sensor(s) to the first signal processing device is diverted, and optionally amplified, for processing by the additional signal processing device(s). The additional signal processing device(s) may be configured to process the PPG signals, and optionally (or alternatively), signals from the auxiliary respiration sensor, to determine at least one physiological parameter or event of the individual. For example, the PPG signals and optionally signals from the auxiliary respiration sensor may be processed to determine a respiratory parameter including, but not limited to, respiration rate and respiratory effort, or a respiratory event including, but not limited to, inspiration, expiration, obstruction, apnea, hypopnea, and hypernea. In some cases, the respiratory parameter or event is a respiratory parameter or event that is not determined by the first signal processing device. In some embodiments, the PPG signals may be processed by the first signal processing device, while the additional signal processing device(s) only process the signals from an auxiliary respiration sensor.

In some embodiments, the additional signal processing device(s) may also process and display the data in real time, which refers to the fact that the signals do not have to be averaged over time but the physiological parameters or events can be communicated to caregivers or the individual at the time of their occurrence or immediately thereafter.

In some embodiments of the invention, the detection of the PPG signals by the additional signal processing device(s) does not disrupt the operation of the first signal processing device. Thus, while a portion of the signals may be detected by the additional signal processing devices, the first signal processing device will operate in the same manner as if the additional signal processing devices were not present. In some cases, when the first signal processing device is disconnected, the additional signal processing devices may automatically take over monitoring the signals previously processed by the first signal processing device. In particular embodiments, at least one physiological parameter monitored by the first signal processing device at a first time point can be monitored by one of the additional signal processing devices after disconnection of the first signal processing device. For example, when a traditional oximeter is the first signal processing device and is disconnected from the sensor(s), the second signal processing device may automatically monitor the blood oxygen saturation of the patient.

In particular embodiments of the invention, the system includes a first signal processing device in electronic communication with the PPG sensor, whereby the PPG sensor transmits PPG signals to the first signal processing device, a second signal processing device that detects at least a portion of the signals transmitted by the PPG sensor to the first signal processing device, at least a portion of signals transmitted by the auxiliary respiration sensor, or both; and a third signal processing device that is in communication with the second signal processing device. The third signal processing device may be independent of the other signal processing devices, and may include at least one of (1) a power source for the second signal processing device and (2) an additional display for a physiological parameter or event. As an example, the first signal processing device may be an oximeter, and the second signal processing device may detect signals to/from a PPG sensor in communication therewith and/or it may detect signals from an auxiliary respiration sensor. The third signal processing device could be a multiparameter monitor. Multiparameter monitors often have powered serial ports (e.g., for capnometry), and the second signal processing device could receive power from the multiparameter monitor, and in some cases, the multiparameter monitor could display and/or process data from the second signal processing device, such as, for example, a respiratory waveform or respiratory parameters.

Any suitable signal processing device may be used for both the first, second or any additional signal processing devices, and such devices include, for example, a general-purpose microprocessor, a digital signal processor (DSP) or application specific integrated circuit (ASIC). While the singular of such terms is used, a "signal processing device" may also include two or more signal processing devices integrated together. Such a microprocessor may be adapted to execute software, which may include an operating system and one or more applications, as part of performing the functions described herein. In electronic communication with the microprocessor may be a computer memory, such as a read-only memory (ROM), random access memory (RAM), and the like. Any suitable computer-readable media may be used in the system for data storage. Computer-readable media are capable of storing information that can be interpreted by microprocessor. This information may be data or may take the form of computer-executable instructions, such as software applications, that cause the microprocessor to perform certain functions and/or computer-implemented methods. Depending on the embodiment, such computer-readable media may include computer storage media and communication media.

Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

Connectivity

The signal processing device(s) may be connected to the sensor(s) in any suitable fashion, but typically they are connected via a wire, cable or other conventional means known in the art. In some embodiments, however, the signal processing device(s) may be connected to the sensor(s) via wireless communication, including but not limited to, Bluetooth®, WiFi, Zigbee and/or infrared technology.

In particular embodiments of the invention, provided are additional signal processing devices that can detect the signals from more than one sensor, and in some cases, can switch between sensors while remaining in circuit. Thus, a clinician may alternate between a conventional PPG sensor (e.g., a finger pulse oximetry sensor) and another type of sensor, such as those that include a PPG sensor and an auxiliary respiration sensor (e.g., a thermistor). Along with ports (or other communication connectors) for more than one PPG sensor, the additional signal processing devices may be configured to transition between the two (or more) sensors without breaking the circuit. In some embodiments, the two or more PPG sensors may be used at the same time, and the additional signal processing device(s) can process both signal streams. For example, in some cases, it may be desirable to determine blood oxygen saturation at both the peripheral site (e.g., a finger) and a central source site (e.g., nasal alar), as the difference in saturation values at central and peripheral sites may provide physiological information.

EXAMPLES

Figure 1:
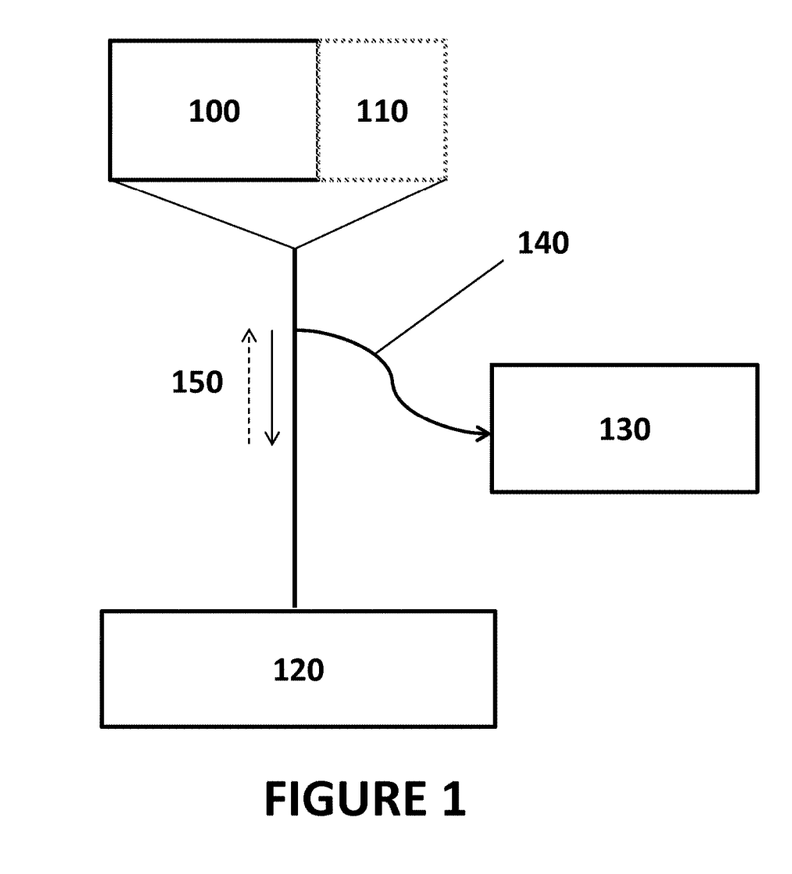
FIG. 1 is a schematic diagram of a system according to an embodiment of the present invention.

Examples of methods of using the system embodiments will now be described with reference to a particular system according to an embodiment of the invention, as shown in FIG. 1. Referring to FIG. 1, a system according to embodiments of the present invention may include a PPG sensor 100, and optionally an auxiliary respiration sensor 110 integrated with or connected thereto. The PPG sensor 100, and optionally the auxiliary respiration sensor 110, transmits PPG signals 150, and optionally the signals from the auxiliary respiration sensor 110, to the first signal processing device 120 and in some cases, the first signal processing device 120 also transmits input signals to the sensor(s). A second signal processing device 130 detects 140 the PPG signals 150 between the PPG sensor 100 and first signal processing device 120 and may further receive signals from the auxiliary respiration sensor 110. In some cases, the second signal processing device 130 further detects 140 at least some of the least input signals sent from the first signal processing device 120 to the PPG sensor 100. For example, in some cases, the first signal processing device 120 sends input signals for energizing an LED in the PPG sensor 100.

Figure 2:
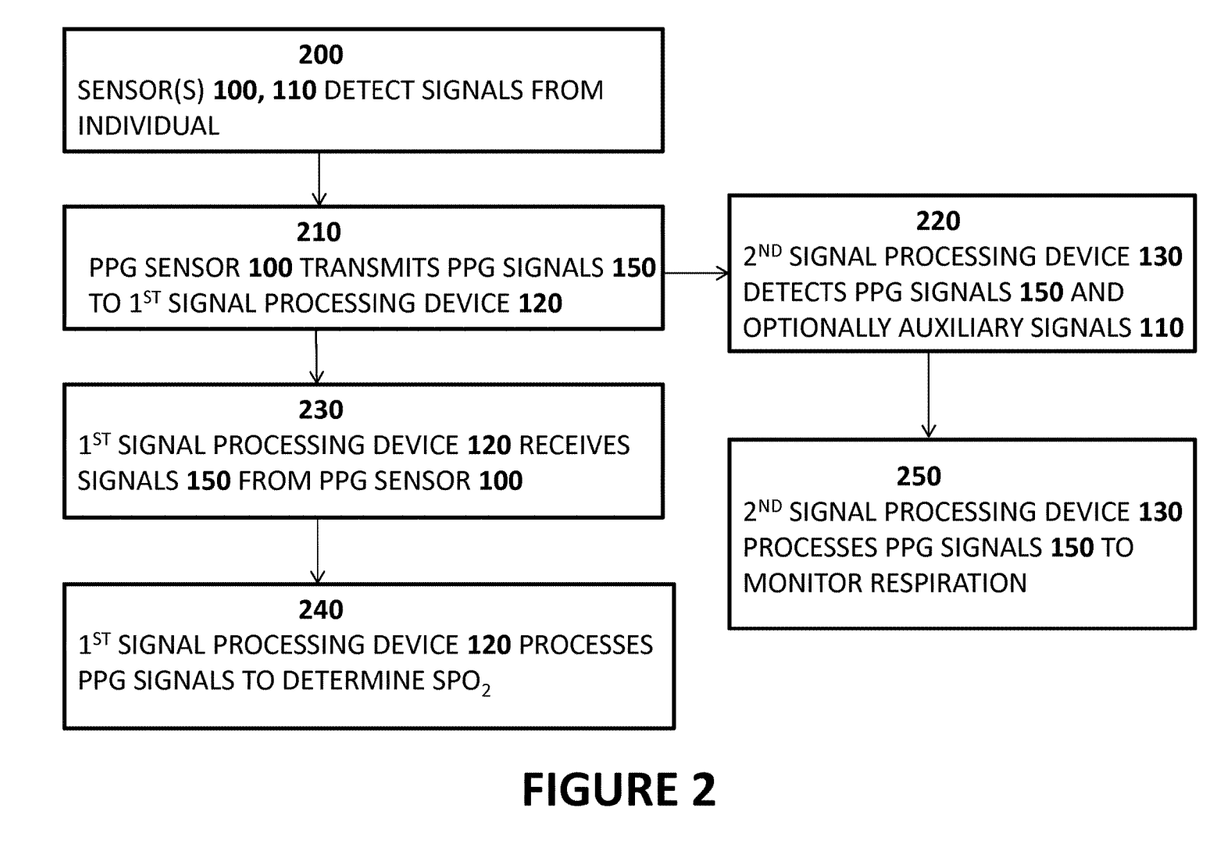
FIG. 2 is a flowchart describing steps performed by the system in FIG. 1 in some embodiments of the invention.

FIG. 2 is a flow chart illustrating method steps according to an embodiment of the invention. In step 200, physiological signals from the individual are detected by the PPG sensor 100 and optionally the auxiliary signal processing device 110. In step 210, the PPG sensor 100 transmits PPG signals 150 to the first signal processing device 120, in step 220, the second signal processing device 130 detects the PPG signals 150, and optionally signals from the auxiliary respiration sensor 110. In step 230, the first signal processing device receives the signals 150 from the PPG sensor 100. In some embodiments, the second signal processing device 130 may be connected to the PPG sensor 100 via the cable connecting the PPG sensor 100 to the first signal processing device 120, such as via a splitter or connector. In step 240, the first signal processing device 120 processes the PPG signals 150 to determine blood oxygen saturation (SpO$_2$)) and/or other physiological parameters. In step 250, the second signal processing device 130 also processes the PPG signals 150 and optionally signals from the auxiliary respiration sensor 110 to determine a respiratory parameter or event, in some cases, the second signal processing device 130 determines at least one physiological parameter or event not determined by the first signal processing device 120.

Figure 3:
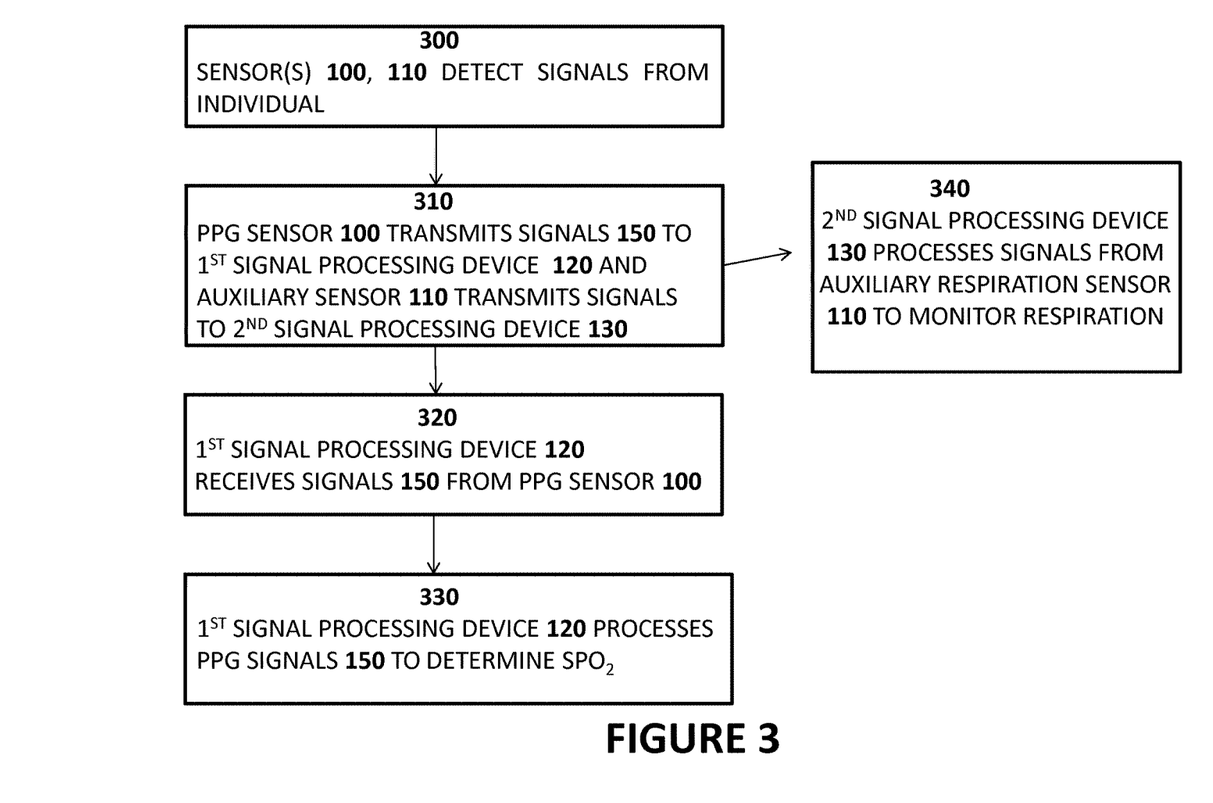
FIG. 3 is a flowchart describing steps performed by the system in FIG. 1 in some embodiments of the invention.

In the previous example, the second signal processing device 130 processes both the PPG signals 150 and the signals from the auxiliary respiration sensor 110. However, in other embodiments, the PPG signals 150 are transmitted only to the first signal processing device 120 and the signals from the auxiliary respiration sensor 110 are transmitted to the second signal processing device 130. Referring to FIG. 3, step 300 describes detecting physiological signals from the PPG sensor 100 and at least one auxiliary respiration sensor 110. In step 310, the PPG sensor 100 transmits PPG signals 150 to the first signal processing device 120 and the at least one auxiliary respiration sensor 110 transmits its signals to the second signal processing device 130. In some cases, the same cable can be used to transmit both the PPG signals 150 and the signals from the auxiliary respiration sensor 110. In some cases, a splitter or connector may be used to divert the signals from the auxiliary respiration sensor 110 to the second signal processing device 130. In step 320, the first signal processing device 120 receives the PPG signals 150 from the PPG sensor 100, and in step 330, the first signal processing device 120 processes the PPG signals 150 to determine physiological parameter such as blood oxygen saturation. In step 340, the second signal processing device 130 processes signals from the auxiliary respiration sensor 110 to monitor respiration in the individual.

Figure 4:
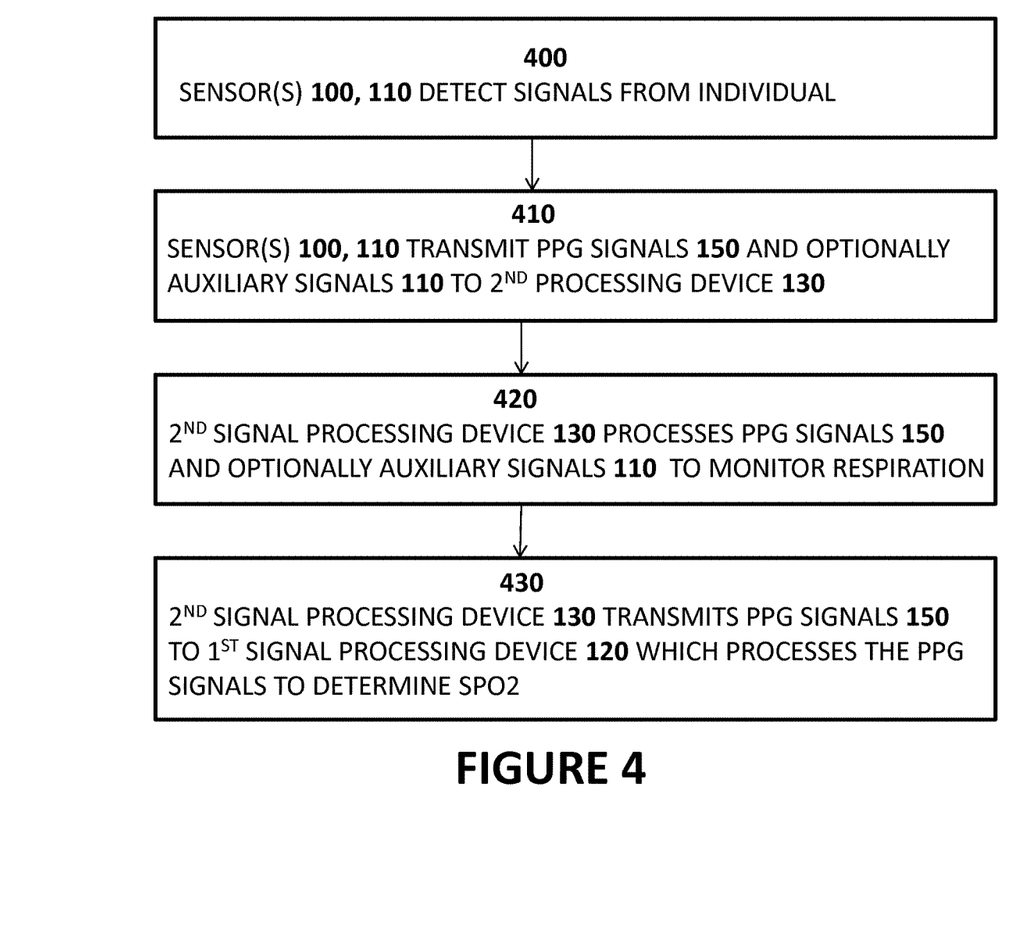
FIG. 4 is a flowchart describing steps performed by the system in FIG. 1 in some embodiments of the invention.

Referring to FIG. 4, in some embodiments of the invention, the second signal processing device 130 receives all of the PPG signals 150 from the PPG sensor, and optionally signals from the auxiliary respiration sensor 110, and then transmits at least some of the PPG signals 150 to the first signal processing device 120. Specifically, in step 400, the sensor(s) 100, 110, detect signals from the individual. In step 410, the sensor(s) transmit PPG signals 150 and optionally signals from the auxiliary respiration sensor 110 to the second signal processing device 130. In step 430, the second signal processing device 130 then transmits the PPG signals 150 and optionally signals from the auxiliary respiration sensor 110 to the first signal processing device 120, which uses the PPG signals 150 to determine physiological parameter such as blood oxygen saturation. In optional step 420, the second signal processing device 130 processes at least some of the PPG signals 150 and optionally signals from the auxiliary respiration sensor 110 to determine a physiological parameter or event. In some embodiments, the second signal processing device 130 processes at least some of the PPG signals 150 and optionally signals from the auxiliary respiration sensor 110 before transmitting the PPG signals 150 to the first signal processing device 120.

Figure 5A:
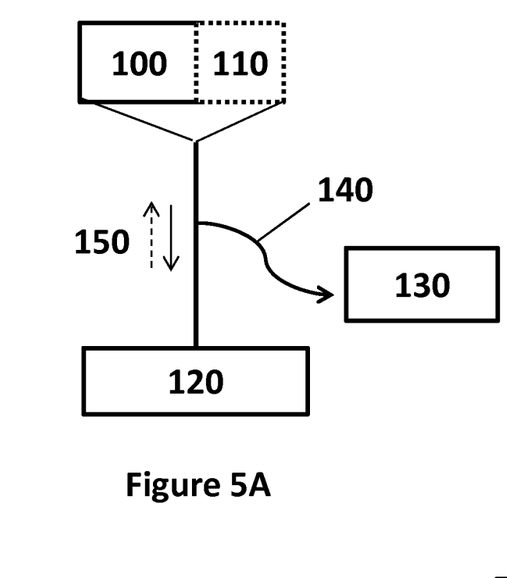
FIG. 5 shows a system according to an embodiment of the invention before disconnecting a first signal processing device (5A) and after disconnecting the first signal processing device (5B).
Figure 5B:
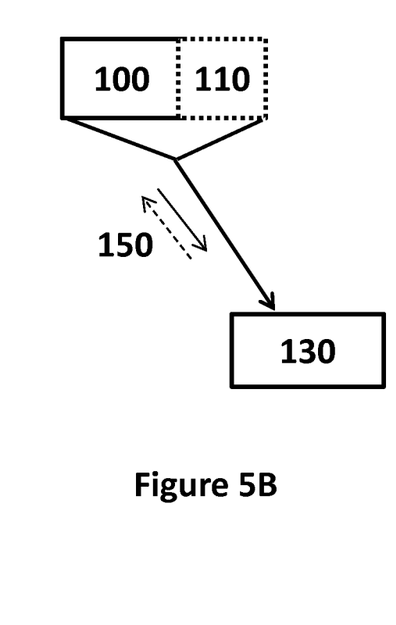

In some embodiments of the invention, the second signal processing device 130 can take over for the first signal processing device 120 when it is disconnected. For example, in some cases, the second signal processing device 130 may include a portable monitor that may be used in transit between different care locations, such as between one hospital department to another, or during emergency transportation services. Thus, when a patient needs to be transferred to a different location, it may be desirable to detach the PPG sensor 100 and optional auxiliary respiration sensor 110 from the first signal processing device 120 to move the patient, and use the second signal processing device 130 to monitor physiological parameters, including, for example, respiration and/or blood oxygen saturation, during transport to the new location. FIG. 5A shows a system diagram for an embodiment wherein the first signal processing device 120 and second signal processing device 130 are both used to monitor the individual (a first time period). FIG. 5B shows the system after detaching the first signal processing device 120, whereby all of the signal(s) 100, 110 are transmitted directly to the second signal processing device 130 (a second time period). In some embodiments, the PPG sensor 100 and optional auxiliary respiration sensor 110 may be reconnected to a new signal processing device (e.g., a conventional monitor in the new location) and the second signal processing device 130 may automatically return to the secondary detection of the PPG signals, 150.

Figure 6:
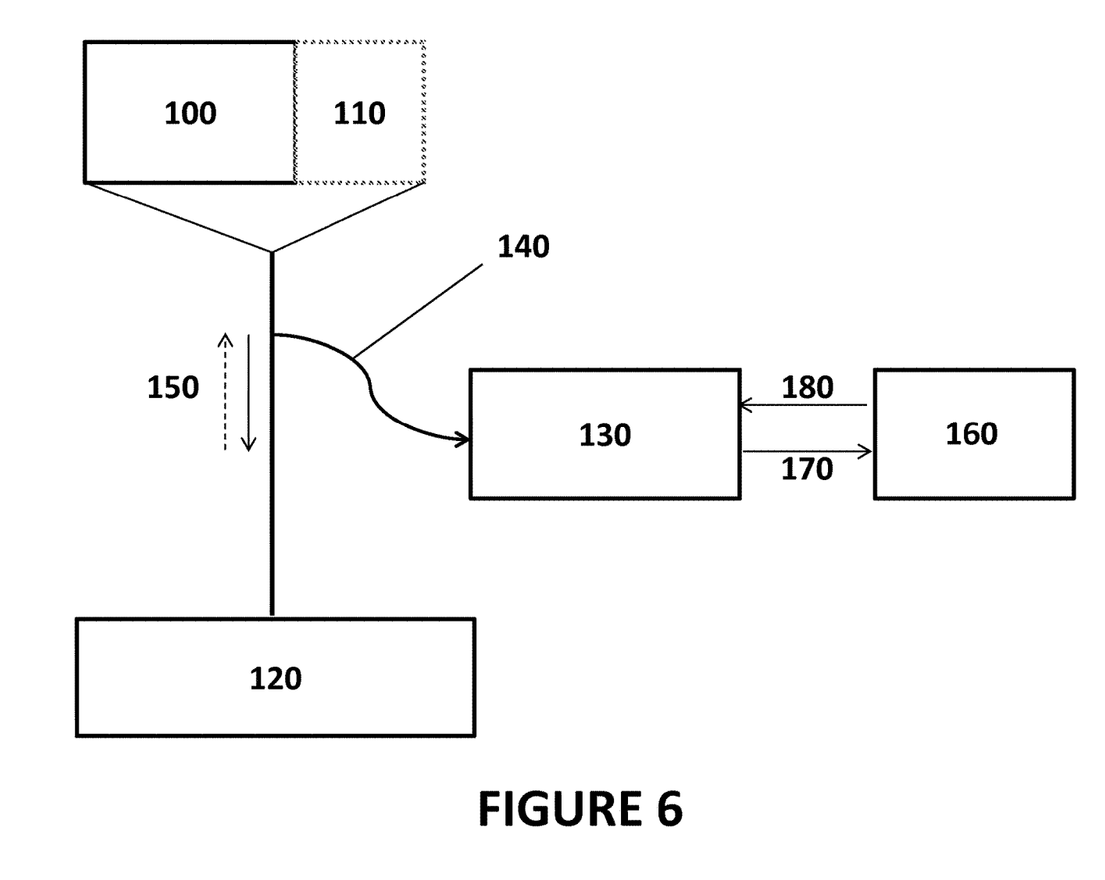
FIG. 6 shows a system according to an embodiment of the invention including a third signal processing device.

Referring to FIG. 6, in some embodiments of the invention, a third signal processing device 160 may be in communication with the second signal processing device 130. In this example, the first signal processing device 100 is an oximeter, and the third signal processing device 160 is a multiparameter monitor. The second signal processing device 130 detects 140 the PPG signals 150 sent from the PPG sensor 110 and/or the signals from the auxiliary respiration sensor 110. The second signal processing device may process at least some of the signals and then transmit 170 the signals to the third signal processing device 160 for further processing and/or display. The third signal processing device 160 may also provide a power supply 180 to the second signal processing device 130. In particular examples, the second signal processing device detects the signals from the auxiliary respiration sensor 100, and optionally the PPG sensor 100 and determines at least one respiratory waveform, parameter or event. The second signal processing device 130 then transmits this respiratory information to the third signal processing device 160, in this case, a multiparameter monitor, for display. The multiparameter monitor 160 has a powered serial port and so may provide a power supply 180 to the second signal processing device 130.

Figure 7:
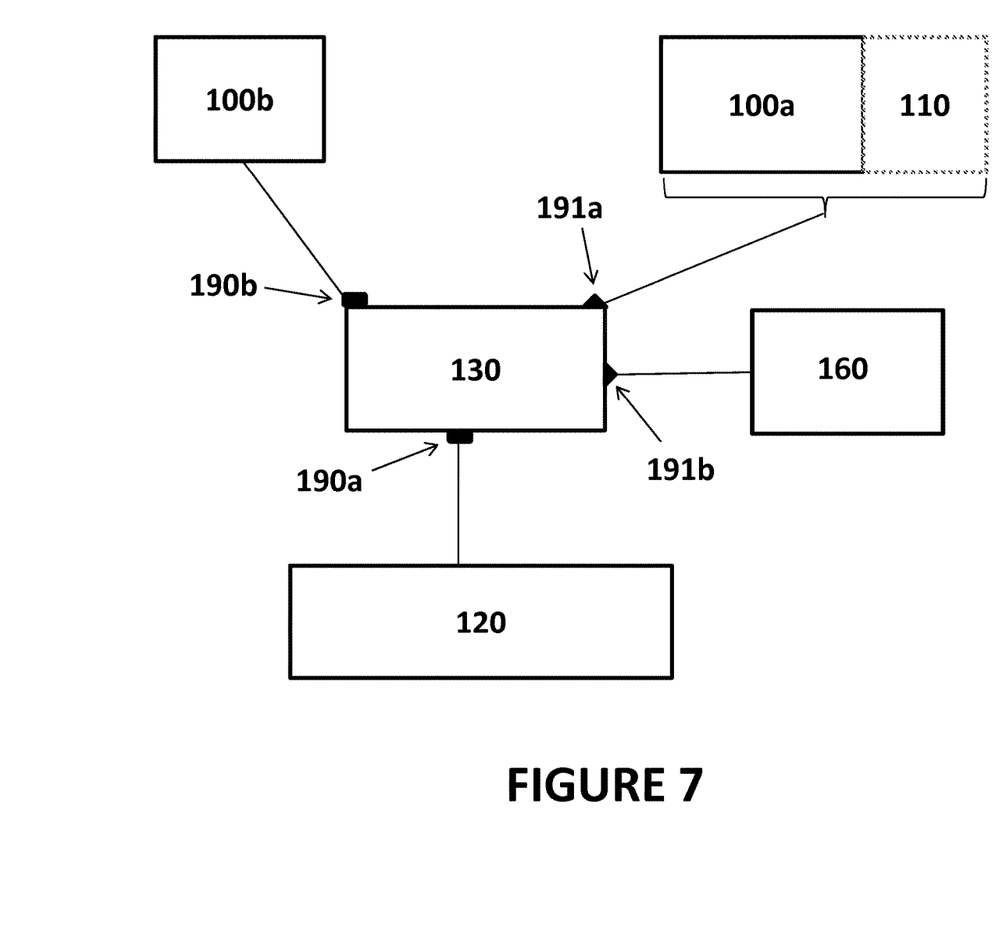
FIG. 7 shows a system according to an embodiment of the invention that includes two PPG sensors connected to the second signal processing device.

Referring to FIG. 7, in some embodiments, the second signal processing device 130 is configured to be able to connect to two (or more) PPG sensors 100a, 100b. In a particular example, the second signal processing device 130 connects to the first signal processing device (in this case an oximeter) 120 via a male DB9 connector 190a and connects to a conventional pulse oximetry sensor 100b through a female DB9 connector 190b. The other pulse oximetry sensor 100a, which is integrated with an auxiliary respiration sensor 110, may be connected to the second signal processing device 130 through a flying lead 191a. A third signal processing device 160, if present, may also be connected to the second signal processing device 130 via a flying lead 191b. Other types of connectors may also be used in lieu of or in addition to those described above.

In the drawings and specification, there have been disclosed embodiments of the invention and, although specific terms are employed, they are used in a generic and descriptive sense only and not for purposes of limitation, the scope of the invention being set forth in the following claims.

We claim:

1. A method of physiological monitoring comprising
securing a PPG sensor to an individual in a first care location;
transmitting a PPG signal stream from the PPG sensor to an oximeter or multiparameter monitor in the first care location,
processing the PPG signal stream being transmitted to the oximeter or multiparameter monitor with a signal splitter so that an identical PPG waveform is transmitted to a portable signal processing device located in the first care location,
processing the PPG waveform of the PPG signal stream with the oximeter or multiparameter monitor to determine a blood oxygen saturation of the individual, whereby the oximeter or multiparameter monitor does not determine at least one of a respiratory rate, a respiratory effort and a respiratory event based on the PPG signals; and processing the identical PPG waveform with the portable signal processing device to determine at least one of a respiration rate, a respiratory effort and a respiratory event of the individual;
ceasing transmission of the PPG signal stream from the PPG sensor to the oximeter or multiparameter monitor at the first care location, and
transporting the individual and the portable signal processing device to a second care location,
whereby the portable signal processing device automatically calculates the blood oxygen saturation of the individual once the PPG sensor ceases transmission of the PPG signal stream from the PPG sensor to the oximeter or multiparameter monitor.

2. The method of claim 1, wherein the portable signal processing device is independent from the oximeter or multiparameter monitor.

3. The method of claim 1, wherein the portable signal processing device amplifies and then processes the identical PPG waveform.

4. The method of claim 1, wherein signals from an auxiliary sensor are transmitted to the portable signal processing device and the signals from the auxiliary sensor and the identical PPG waveform are used to determine the at least one of the respiration rate, the respiratory effort and the respiratory event of the individual.

5. The method of claim 1, wherein the oximeter or multiparameter monitor is integrated with or in communication with a first display monitor and the portable signal processing device is integrated with or in communication with a second display monitor.

6. The method of claim 1, wherein the portable signal processing device further detects input signals for energizing a light emitting diode in the PPG sensor transmitted by the oximeter or multiparameter monitor to the PPG sensor.

7. The method of claim 1, wherein the portable signal processing device is in communication with a third signal processing device, and the third signal processing device displays the at least one of the respiration rate, the respiratory effort and the respiratory event determined by the identical PPG waveform.

8. The method of claim 7, wherein the third signal processing device provides a power input for the portable signal processing device.

* * * * *